(12) United States Patent
Kolter et al.

(10) Patent No.: US 9,763,888 B2
(45) Date of Patent: Sep. 19, 2017

(54) RAPIDLY DISPERSIBLE, FINE-PARTICLE FILM-COATING COMPOSITION WHICH IS IN POWDER FORM, IS NOT PRONE TO SEGREGATION AND IS BASED ON POLYVINYL ALCOHOL-POLYETHER GRAFT COPOLYMERS CHARACTERIZED BY PARTICULAR PHYSICAL STABILITY AND LOW ASPERITY

(75) Inventors: Karl Kolter, Limburgerhof (DE); Maximilian Angel, Schifferstadt (DE); Andreas Habich, Speyer (DE)

(73) Assignee: BASF SE, Ludwigshafen (DE)

( * ) Notice: Subject to any disclaimer, the term of this patent is extended or adjusted under 35 U.S.C. 154(b) by 1043 days.

(21) Appl. No.: 11/631,368

(22) PCT Filed: Jun. 22, 2005

(86) PCT No.: PCT/EP2005/006718
§ 371 (c)(1),
(2), (4) Date: Dec. 29, 2006

(87) PCT Pub. No.: WO2006/002808
PCT Pub. Date: Jan. 12, 2006

(65) Prior Publication Data
US 2008/0044469 A1    Feb. 21, 2008

(30) Foreign Application Priority Data
Jun. 30, 2004  (DE) .................. 10 2004 031 835

(51) Int. Cl.
| A61K 9/28 | (2006.01) |
| A61K 47/32 | (2006.01) |
| A61K 9/16 | (2006.01) |
| A61K 9/48 | (2006.01) |

(52) U.S. Cl.
CPC ............ A61K 9/2853 (2013.01); A61K 9/284 (2013.01)

(58) Field of Classification Search
None
See application file for complete search history.

(56) References Cited

U.S. PATENT DOCUMENTS

| 4,683,256 | A | * | 7/1987 | Porter et al. ................ 524/285 |
| 4,981,882 | A | * | 1/1991 | Smith et al. ................. 523/205 |
| 5,258,436 | A | * | 11/1993 | Wheatley et al. ............ 524/388 |
| 5,811,082 | A | * | 9/1998 | Ahlnas et al. ................. 424/59 |
| 6,413,590 | B1 | | 7/2002 | Anderson et al. |
| 6,579,953 | B1 | | 6/2003 | Gotsche et al. |
| 2002/0177579 | A1 | * | 11/2002 | Augsburger et al. ......... 514/102 |
| 2005/0107498 | A1 | * | 5/2005 | Kolter et al. ................. 524/35 |

FOREIGN PATENT DOCUMENTS

| DE | 1077430 | 3/1960 | |
| DE | 1081229 | 5/1960 | |
| DE | 1094457 | 12/1960 | |
| GB | 922457 | 1/1963 | |
| GB | 922458 | 4/1963 | |
| GB | 922459 | 4/1963 | |
| WO | WO00/18375 | 4/2000 | |
| WO | WO01/04195 A1 | 1/2001 | |
| WO | WO03/070224 A1 | 8/2003 | |
| WO | WO 03070224 A1 * | 8/2003 | .............. A61K 9/28 |

* cited by examiner

*Primary Examiner* — Susan Tran
*Assistant Examiner* — William Craigo
(74) *Attorney, Agent, or Firm* — Drinker Biddle & Reath LLP

(57) ABSTRACT

A rapidly dispersible, fine-particle film-coating composition which is in powder form and is not prone to segregation for coating pharmaceutical dosage forms, consisting of
a) 40-90% by weight of a polyvinyl alcohol-polyether graft copolymer (component A),
b) 1-20% by weight of a polyvinylpyrrolidone or of a vinylpyrrolidone-vinyl acetate-copolymer with a K value of from 10 to 100 (component B)
c) 10-60% by weight of organic or inorganic pigments having an average particle size of less than 8 μm (component C)
d) 0.5-15% by weight of a surfactant having an HLB of greater than 10 (component D) and
e) 0-30% by weight of further customary coating ingredients (components E),
in which the particles of component C are embedded in a coherent polymer matrix,
where the total amount of components A to E is 100% by weight.

43 Claims, No Drawings

RAPIDLY DISPERSIBLE, FINE-PARTICLE FILM-COATING COMPOSITION WHICH IS IN POWDER FORM, IS NOT PRONE TO SEGREGATION AND IS BASED ON POLYVINYL ALCOHOL-POLYETHER GRAFT COPOLYMERS CHARACTERIZED BY PARTICULAR PHYSICAL STABILITY AND LOW ASPERITY

This application is the National Phase of International Application No. PCT/EP2005/006718 filed on Jun. 22, 2005; and this application claims priority of Application 102004031835.2 filed in Germany on Jun. 30, 2004 under 35 U.S.C. §119; the entire contents of all are hereby incorporated by reference.

The present invention relates to rapidly dispersible film coatings for coating pharmaceutical dosage forms or dietary supplements, which consist of at least one polyvinyl alcohol-polyether graft copolymer (component A), a polyvinylpyrrolidone or vinylpyrrolidone-vinyl acetate copolymer (component B), organic or inorganic pigments having an average particle size of less than 8 μm (components C), a surfactant with an HLB of greater than 10 (component D) and further conventional coating ingredients. The invention further relates to particular processes for the production of dry coating premixes, where the components are firmly associated together and show no segregation at all, and of aqueous coating suspensions, and the application thereof to solid dosage forms.

Solid dosage forms are provided with a rapidly dissolving coating for a wide variety of reasons. Thus, for example, it is possible to improve the appearance, the distinguishability and the swallowability, to mask a bitter taste or to protect the dosage form from external influences such as, for example, moisture or oxygen. Since the film coating is intended to dissolve rapidly in various aqueous media, inter alia in simulated gastric and intestinal fluids, the most important ingredient of the coating preparation must be a water-soluble, film-forming polymer. The film-forming polymers employed for coating tablets are mainly hydroxypropylmethylcellulose and hydroxypropylcellulose, but they have serious disadvantages. Thus, the viscosity of these polymers in water is very high and permits a concentration of only up to about 10%, because the high viscosity at higher concentrations means that fine atomization in the spray nozzle is no longer possible, and the coating is rough, inhomogeneous and unsightly. In addition, these polymers are very brittle and frequently develop cracks during storage, especially if the core changes in volume through uptake or release of moisture.

Polyvinyl alcohol is likewise known as film former, but is rarely employed because of various disadvantages. The use of polyvinyl alcohol-containing preparations consisting of polyvinyl alcohol, plasticizer and talc is described in WO 01/04195. The disadvantages of these preparations are the slow dissolution when the aqueous coating solution is prepared, the high viscosity, the low concentration in the spraying solution, the use of plasticizers and the slow rate of dissolution of the film coating, especially after storage, and embrittlement of the film coating after storage associated with the formation of cracks. In addition, when more concentrated polyvinyl alcohol solutions (>8%) are sprayed there is thread formation at the spray nozzle.

The use of polyvinyl alcohol-polyether graft copolymers as coating agents or binders in pharmaceutical dosage forms or as packaging material or as additive in cosmetic dermatological or sanitary preparations is disclosed for example in WO 00/18375. Thus, for example, a formula for a film-coating composition which consists of a polyvinyl alcohol-polyether graft copolymer and the usual coating ingredients for coloring and opacity, namely iron oxide, talc and titanium dioxide is described. Although a coating of this type is flexible, it is relatively soft and shows signs of abrasion when shear forces act on it. This is important in particular with very large coating batches, because in such cases the high pressure caused by the height of the bed of tablets in conjunction with the rolling motion of the tablets in the drum generates correspondingly high shear forces. Since many medicinal substances and also some excipients are very lipophilic, the coatings frequently adhere poorly to the tablet surface. In addition, the smoothness and gloss of such coating preparations are unsatisfactory.

WO 03/070224 describes coatings consisting of polyvinyl alcohol-polyether graft copolymers, of a component having hydroxy, amide or ester functions and of further usual coating ingredients. In this case there is initial production of a premix of the starting materials as physical mixture, and the latter is then dispersed in water. These preparations are prone to segregation and their asperities are not good.

It is an object of the present invention to develop a film coating which in the form of a powder does not lead to any segregation of the individual ingredients, in particular of pigments and polymers, which has excellent flow characteristics, which can be dissolved or suspended very easily and rapidly in water, resulting in a very short time to produce the preparation for spraying, which can be sprayed with high polymer and solids concentrations and with a high spraying rate without the spray nozzle becoming blocked, which spreads very well on the surface, which is flexible and forms no cracks during storage, which is not tacky, which adheres well to all surfaces, which exhibits excellent smoothness and gloss, which is very stable to mechanical stress, and which dissolves very rapidly.

We have found that this object is achieved by film-coating compositions in powder form, consisting of
a) 40-90% by weight of a polyvinyl alcohol-polyether graft copolymer (component A),
b) 1-20% by weight of a polyvinylpyrrolidone or of a vinylpyrrolidone-vinyl acetate-copolymer (component B)
c) 10-60% by weight of organic or inorganic pigments having an average particle size of less than 8 μm (component C)
d) 0.5-15% by weight of a surfactant having an HLB of greater than 10 (component D) and
e) 0-30% by weight of further customary coating ingredients (components E),
in which component C is embedded in a coherent polymer matrix,
where the total amount of components A to E is 100% by weight.

Polyvinyl alcohol-polyether graft copolymers mean polymers which are obtainable by polymerizing
a) at least one vinyl ester of aliphatic $C_1$-$C_{24}$-carboxylic acids preferably vinyl acetate, in the presence of
b) polyethers of the general formula I,

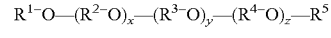

c) in which the variables have independently of one another the following meaning:
R$^1$ hydrogen, $C_1$-$C_{24}$-alkyl, R$^6$-C(=O)—, polyalcohol residue;

preferably: $R_1$=H, $CH_3$—
$R^5$ hydrogen, $C_1$-$C_{24}$-alkyl, $R^{6-}C(=O)$—;
  preferably: $R^5$=H
$R^2$ to $R^4$
  —$(CH_2)_2$—, —$(CH_2)_3$—, —$(CH_2)_4$—, —$CH_2$—CH($CH_3$)—,
  —$CH_2$—CH($CH_2$—$CH_3$)—, —$CH_2$—CHOR$^{7-}$CH$_2$—;
  preferably $R_2$ to $R_4$: —$(CH_2)_2$—, —$CH_2$—CH($CH_3$)—
  very particularly preferably $R_2$ to $R_4$: —$(CH_2)_2$—
$R_6$ $C_1$-$C_{24}$-alkyl;
$R_7$ hydrogen, $C_1$-$C_{24}$-alkyl, $R^{6-}C(=O)$—;
x 1 to 5000;
  preferably: x=10 to 2000;
  very particularly preferably: x=20 to 500
y 0 to 5000;
  preferably: y=0
z 0 to 5000;
  preferably: z=0,
  with the proviso that x≥10 when y and z=0,
and subsequent complete or partial hydrolysis of the polyvinyl ester groups.

x, y, z:
  calculation of the molecular weight of the polyether from x, y and z results in an average, because corresponding products usually have a broad distribution of molecular weight.

Preferred polyethers have an average molecular weight between 400 and 50 000 g/mol, particularly preferably from 1500 to 20 000 g/mol.

The preparation of such graft copolymers is known per se.

DE 1 077 430 describes a process for preparing graft polymers of vinyl esters on polyalkylene glycols.

DE 1 094 457 and DE 1 081 229 describe processes for preparing graft polymers of polyvinyl alcohol on polyalkylene glycols by hydrolyzing the vinyl esters and the use thereof as protective colloids, water-soluble packaging films, as sizes and finishes to textiles and in cosmetics.

Preferred polymers have a degree of hydrolysis of the polyvinyl ester groups of >70 mol %,
particularly preferably >80 mol % and
very particularly preferably of >85 mol %.

A particularly preferred polyvinyl alcohol-polyether graft copolymer is one in which
a) vinyl acetate has been used as monomer for grafting,
b) the variables have the following meaning:
  $R^1$=H
  $R^2$-$R^4$=—$(CH_2)_2$—
  $R_5$=H
  x=20 to 500
  y=0
  z=0
  and thus represent a polyethylene glycol with an average molecular weight of 6000
c) the degree of hydrolysis of the ester groups is >85 mol %, and
d) the mass ratio of the polyvinyl alcohol/polyethylene glycol 6000 moieties is 75:25.

In addition, the film-coating compositions comprise as components B a polyvinylpyrrolidone or a vinylpyrrolidone-vinyl acetate copolymer. The Fikentscher K value, measured in water, of these polymers is between 10 and 100, preferably between 12 and 60 and particularly preferably between 20 and 50.

The film-coating compositions further comprise as components C organic or inorganic pigments having an average particle size of less than 8 μm, preferably <6 μm, particularly preferably <4 μm. The lower limit of the average particle size is generally 0.5 μm.

Reference to pigments means coloring or white substances which are not soluble in the application medium.

Suitable inorganic pigments are aluminum silicates, magnesium silicates, magnesium-aluminum silicates, iron oxide, titanium dioxide, zinc oxide, silica, or calcium hydrogen phosphate. Of the aluminum silicates, kaolin is particularly suitable. Of the magnesium silicates, talc is particularly important. Preferred pigments are iron oxide and white pigments selected from the group consisting of titanium dioxide, talc and kaolin.

Suitable organic pigments are organic lakes or mixtures thereof. Examples of organic lakes which can be used are: quinoline yellow lake, tartrazine lake, orange-yellow lake, FD&C yellow aluminum lake, cochineal red lake, erythrosine lake, azorubine lake, indigotine lake, beta-carotene.

Surfactants with an HLB (hydrophilic lipophilic balance; cf. Fiedler, Lexikon der Hilfsstoffe, Editio Cantor Verlag Aulendorf, 5th edition (2002), pages 115-121) greater than 10 are employed as components D.

Those particularly suitable are alkali metal salts of C8-C30 fatty acids, C8-C30 alkylsulfonates, C8-C30-alkyl sulfates, C8-C30-alkylarylsulfonates or dioctyl sulfosuccinate, ethoxylates of C8-C30-fatty acids, C8-C30-fatty alcohols, fatty acid glycerides, sorbitan fatty acid esters, sorbitan fatty alcohol ethers or phenols, and polyoxypropylene-polyoxyethylene block copolymers. Examples from the classes of substances mentioned are sodium stearate, sodium oleate, sodium laurylsulfonate, sodium laurylsulfate, polyoxyethylene (9) monostearate, polyoxyethylene (10) stearyl/cetyl ether, polysorbate 80, polysorbate 20, ethoxylated castor oil (35 EO), ethoxylated hydrogenated castor oil (40 EO), ethoxylated 12-hydroxystearic acid (15 EO), poloxamer 188, poloxamer 408.

The film coatings may further comprise as components E additional excipients as are customary as coating ingredients. Further customary coating ingredients include: water-soluble colorants, non-stick agents, fillers, gloss improvers, antifoams, protective colloids, buffer substances, pH-regulating substances, bonding agents or plasticizers.

The preparations of the invention are produced by intensive grinding and homogenization of the pigments to a high degree of fineness and by drying. The grinding is carried out in aqueous solution employing mills or high-shear dispersing units. Those particularly suitable are ball mills, corundum disk mills, rotor-stator units or high-pressure homogenizers. It is important in this connection for the pigments to be reduced to an average particle size of less than 8 μm, preferably less than 6 μm, particularly preferably less than 4 μm. The grinding in aqueous solution, especially in the presence of further ingredients of the preparations of the invention, which may act as protective colloid or wetting aid, such as polyvinylpyrrolidone, vinylpyrrolidone-vinyl acetate copolymers or surfactants with an HLB of greater than 10, prevents reagglomeration. The subsequent spray drying fixes the degree of fineness.

Production can be carried out by grinding component C in water to the required particle size, combining with the other components and, where appropriate, water, and drying to a powder or granules.

An alternative production procedure consists of grinding component C in water in the presence of component A, component B, component D or component E or combinations thereof to the required particle size, combining with the remaining components and, where appropriate, water, and drying to a powder or granules.

It is also possible to grind component C in water in the presence of components B and D and, where appropriate, E to the required particle size, to combine with an aqueous solution of component A and, where appropriate, component E and water, and to dry to a powder or granules.

A particular embodiment comprises grinding component C in water in the presence of total quantities or partial quantities of components A, B, D or E or combinations thereof to the required particle size, drying to a powder or granules, and mixing with the remaining quantities of component A, B, D and E in powder form and, where appropriate, compacting, extruding, pelleting or granulating.

The quantity of water employed is chosen in the described procedures so that the resulting aqueous dispersions of the film-coating compositions of the invention have solids contents of from 5 to 60, preferably 15 to 50, % by weight.

The aqueous dispersions are preferably dried in a spray dryer, paddle dryer or fluidized bed dryer. The dispersion to be dried is usually pressure-atomized and dried by hot air.

The pressures used for atomizing the suspension for the drying are greater than 0.1 MPa, preferably greater than 2.0 MPa, particularly preferably greater than 8.0 MPa. The atomization can take place using single-fluid nozzles, twin-fluid nozzles or using rotating disks.

The inlet air temperatures for the drying are 50-200° C., preferably 80-180° C.

The film-coating compositions of the invention are attained as powders having average particle sizes of >50 μm, preferably >100 μm, particularly preferably >150 μm. The upper limit of the average particle size is <1000 μm.

The film-coating compositions of the invention are distinguished by the particles of component C being embedded in a coherent polymer matrix. Coherent means that the matrix forms a continuous phase. The individual pigment particles are completely surrounded by polymer or embedded in the polymer matrix. The polymer matrix is formed by polymeric components A and B. The other components D and E are homogeneously dispersed in this matrix. This corresponds to a so-called "solid dispersion", in which the polymer matrix forms the external phase, and the pigment particles form the internal phase. The powder particles thus consist of a polymer matrix in which the pigment particles are dispersed.

On redispersion of the preparations in water for coating pharmaceutical dosage forms, the water-soluble polymers and the other water-soluble ingredients dissolve, and the original degree of fineness is retained. In this aqueous dispersion of the film-coating composition, the aqueous solution then forms the external phase, and the pigment particles form the internal phase, with the particle size of <8 μm for the pigment particles being retained.

The preparations of the invention differ in this way considerably from those customary to date, in which the ingredients are present separately and juxtaposed and may separate or reagglomerate.

In dry form, the preparations of the invention are extremely stable to vibrations and stresses like those normally occurring during the handling of solids, e.g. pouring, setting, filling, transporting. There is no separation of the individual ingredients at all, i.e. no segregation. The individual components cannot be separated by sieving or sifting. The preparation is thus always homogeneous and, on weighing, always quantities with identical ratios are weighed.

The film-coating compositions of the invention can initially be produced as white preparation to which it is later possible to add further coloring components in powder form. The positive properties of the film coatings are retained even with this procedure.

These formulations can where appropriate be compacted, extruded, pelleted or granulated.

For use, the preparations of the invention are stirred into water, mixed where appropriate with further additions, in particular coloring additions, and applied to the substrate by means of a suitable spraying device, with successive drying of the film coating by feeding in heated air. This redispersion requires no high-shear stirring implements but merely simple slow-speed stirrers. The redispersion time is extremely short, and no air is incorporated owing to the low shear, so that no foam is produced. The redispersion is usually complete after 10 min at the latest, and frequently after only 5 min.

Because of the fineness of the pigments and no tendency to reagglomeration, these dispersions are very stable to sedimentation. Even if the stirring is interrupted, no separation of the ingredients occurs. This is surprising because the viscosity of the dispersion is very low. Owing to this stability there is avoidance of blocking of the spraying nozzle or supplying tubing, which occurs at relatively short intervals with conventional preparations. Owing to the stability to sedimentation, no product is deposited on or in the atomizing unit. In addition, the low viscosity makes particularly fine atomization possible. In particular, there is no occurrence of large drops which have an adverse effect on the smoothness, gloss and surface texture. Owing to the low viscosity, the dispersions can be highly concentrated, thus greatly reducing the spraying time. The preparations of the invention therefore combine in a particular manner fineness of particles, viscosity, redispersion rate, stability to sedimentation and sprayability.

The preparations result in films of exceptional quality on the surface of pharmaceutical dosage forms. The fineness of the particles and the good atomizability result in low asperity and good gloss. Despite a high pigment content, the elasticity of the films is high, thus avoiding the formation of cracks on the dosage forms. The elongation at break ordinarily exceeds 20%, preferably 30%. Owing to the particular composition, the films dissolve more rapidly than conventional ones. This is particularly important for medicaments which are intended to act rapidly. In these cases there should be no delay. Normally, the films dissolve in less than 2 min, mostly in less than 1 min.

The high rate of dissolution additionally results in better cleanability of the coating equipment used. The cleaning process can be carried out with simple cleaning compositions and is considerably more rapid than with hydroxypropylmethylcellulose- or polyvinyl alcohol-based coatings. In particular, the preparations of the invention make it possible for the cleaning to be so-called cleaning in place.

The tackiness of the films is very low in the dry and in the moist state. There are no tendencies to adhesion, either during the spraying process of thereafter during further processing or storage.

The coating preparations of the invention adhere better to the dosage forms to be coated. This makes it possible in particular to coat very lipophilic surfaces such as tablets which comprise relatively large amounts of lipophilic active ingredients, wax or fats. Normal coating preparations fail in such cases because the coating solution spreads poorly and adheres poorly. The good spreading properties are achieved in particular through the use of a surfactant with an HLB of greater than 10 in combination with the two polymers.

The excellent wetting properties are also evident in the excellent homogeneity of the coating. Even with thin coatings and high solids concentrations there are no so-called pigment pockets which are attributable to local high colorant concentrations.

These film coatings are smooth and glossy even with very high pigment and solids contents. The imprint is reproduced extremely well. There is no bridge formation or accumulation of solids in the imprint. The coated dosage forms have an excellent appearance.

The oxygen permeability of the preparations of the invention is low, thus making it possible to protect oxygen-sensitive active ingredients in the core better. In addition, the reduced oxidative degradation increases the stability of the colorants employed.

It may be emphasized once again at this point that the preparations of the invention require no plasticizers. Freedom from plasticizers is an enormous advantage because plasticizers often lead to problems during storage of coated forms.

Thus, the plasticizer in the core may migrate and change the physical and chemical properties of the active ingredient, and the film thus becomes brittle and is prone to form cracks. Most plasticizers additionally have a certain volatility which likewise leads to embrittlement. All these disadvantages are absent from the coatings of the invention.

The film coating can be applied in all coating facilities suitable for solid pharmaceutical dosage forms and dietary supplements, such as, for example, horizontal drum coaters, fluidized bed coaters, dip coaters, coating pans.

The coating preparation is atomized preferably using a twin-fluid nozzle. The inlet air temperature should be between 30 and 90° C., preferably between 40 and 80° C.

It is possible in principle for all shapes of cores with curved, convex or concave surfaces to be coated, irrespective of whether the forms are round, polygonal, oblong or football-shaped.

The low viscosities, excellent wetting and spreading properties result in a unique lining of the imprint. No bridging or blurring effects occur in the imprint.

The core may also have a subcoating which is usually applied for special protection of the active ingredient, e.g. from water, oxygen, protons or chemical substances in the coating and in the contents of stomach and intestines.

A further film coating of differing composition can also be applied to the film coating of the invention. Thus, for example, a colorless film coating or a particular glossy layer can be applied.

Concerning the active ingredients, there are no restrictions for the dosage forms of the invention. It is possible to employ active ingredients of all areas of indication, human medicinal substances and veterinary medicinal substances, vitamins, carotenoids, nutraceuticals, dietary supplements, minerals, micronutrients, etc. The active ingredients may have different physicochemical properties such as lipophilicity, solubility, particle size, particle structure, surface etc.

The dosage forms to be coated may be in the form of tablets, capsules or extrudates.

EXAMPLES

The percentage data relate, unless indicated otherwise, to % by weight.

The statements about particle sizes relate to average particle sizes. The particle sizes were determined by laser diffraction, using the D[4,3] value for the analysis.

The resistance to crushing was determined in a Krämer automatic tablet tester.

The friability was determined in an Erweka Friabilator for 4 min at 25 rpm.

The disintegration time was determined as specified in the European Pharmacopoeia. The release was likewise determined as specified in the European Pharmacopoeia.

Example 1

Composition of the Film Coating:

| | |
|---|---|
| Polyvinyl alcohol-polyethylene glycol 6000 (75:25) graft copolymer (degree of hydrolysis 94 mol %) | 60% |
| Vinylpyrrolidone-vinyl acetate 6:4 copolymer (copolyvidone) | 10% |
| Talc | 20% |
| Titanium dioxide | 9% |
| Sodium lauryl sulfate | 1% |

Production:

All the ingredients were stirred into water, using a paddle stirrer, in direct succession in the sequence listed above to result in a solids concentration of 25%. This dispersion was ground using a Skandex ball mill with 0.6-1.25 mm milling elements to an average particle size of the pigment particles of 3.5 μm and then spray dried with an inlet air temperature of 130° C. to result in a free-flowing powder with a particle size of 105 μm.

Use 150.0 g of the preparation were stirred by means of a paddle stirrer into 450.0 g of water. The dissolution or dispersion was complete after 8 min. The spray suspension was of low viscosity and homogeneous. The particle size of the pigment particles after redispersion was 3.1 μm.

The spray suspension was sprayed in a horizontal drum coater (24" Accela-Cota) onto 5 kg of furosemide tablets of the following composition:

| | |
|---|---|
| Furosemide | 40 mg |
| Ludipress ® (BASF AG) [1] | 97.5 mg |
| Copolyvidone | 12.5 mg |
| Microcrystalline cellulose [2] | 97.5 mg |
| Magnesium stearate | 2.5 mg |
| Total weight | 250 mg |
| Diameter: 9 mm, biconvex | |

[1] Formulated product of 93% by weight lactose, 3.5% by weight povidone K30 and 3.5% by weight crospovidone
[2] Average particle size 100 μm Spraying Conditions:

| | |
|---|---|
| Inlet air temperature | 65° C. |
| Outlet air temperature | 33° C. |
| Spraying rate | 50 g/min |
| Spraying pressure | 0.4 MPa |
| Amount applied | 600 g of spray dispersion, equivalent to 150 g of solid |
| Spraying time | 12 min |

Film-Coated Tablet Properties:

| | |
|---|---|
| Resistance to crushing | 105N |
| Friability | 0% |

| | |
|---|---|
| Disintegration time | 3:25 (min:s) |
| Release | 20 min: 100% |

The coating was smooth, uniform and homogeneous. The imprint was nicely reproduced without blurring effects or bridge formation. No prolongation of the disintegration time or of active ingredient release compared with the uncoated tablet core was to be found. The resistance to crushing was 21 N higher than for the uncoated core. No changes in the properties of the film-coated tablets were found during a stability test lasting 12 months.

Example 2

Composition of the Film Coating:

| | |
|---|---|
| Polyvinyl alcohol-polyethylene glycol 6000 (75:25) graft copolymer (degree of hydrolysis 94 mol %) | 61% |
| Vinylpyrrolidone-vinyl acetate 6:4 copolymer (copolyvidone) | 7% |
| Kaolin | 16% |
| Titanium dioxide | 14% |
| Sodium lauryl sulfate | 2% |

Production:

0.7 kg of copolyvidone were dissolved in 6.3 kg of water and then 1.6 kg of kaolin and 1.4 kg of titanium dioxide were introduced. This coarse dispersion was ground in a Coruma-type rotor-stator dispersing unit for 3 h to result in an average particle size of 2.0 µm. This pigment suspension was introduced into a stirred solution of 6.1 kg of polyvinyl alcohol-polyethylene glycol graft copolymer and 0.2 kg of sodium lauryl sulfate in 17.3 kg of water. Spray drying took place at an inlet air temperature of 140° C., with the fines being removed from the spray-dried powder and blown in again in front of the spray nozzle to result in agglomeration and a coarser particle size (agglomerating spray drying or FSD technology). The film-coating compositions were obtained as free-flowing powders with particle sizes of 210 µm.

Use

This preparation was stirred using a paddle stirrer into water to result in a spray preparation with a solids content of 30%. Dissolution or dispersion was complete after 6 min. The spray suspension was of low viscosity and homogeneous. The particle size of the pigment particles after redispersion was 1.7 µm.

The spray suspension was sprayed in a horizontal drum coater (24" Accela-Cota) onto 5 kg of Ambroxol HCl tablets:

Spraying Conditions:

| | |
|---|---|
| Inlet air temperature | 75° C. |
| Outlet air temperature | 37° C. |
| Spraying rate | 60 g/min |
| Spraying pressure | 0.4 MPa |
| Amount applied | 600 g of spray dispersion, equivalent to 180 g of solid |
| Spraying time | 10 min |

Film-Coated Tablet Properties:

| | |
|---|---|
| Resistance to crushing | 107N |
| Friability | 0% |
| Disintegration time | 2:23 (min:s) |
| Release | 20 min: 100% |

The coating was smooth, uniform and homogeneous. The imprint was nicely reproduced without blurring effects or bridge formation. No prolongation of the disintegration time or of active ingredient release compared with the core was to be found. The resistance to crushing was 25 N higher than for the core. No changes in the properties of the film-coated tablets were found during a stability test lasting 12 months.

Example 3

Composition of the Film Coating:

| | |
|---|---|
| Polyvinyl alcohol-polyethylene glycol 6000 (75:25) graft copolymer (degree of hydrolysis 94 mol %) | 40% |
| Polyvinylpyrrolidone of K value 30 | 18% |
| Kaolin | 30% |
| Titanium dioxide | 10.5% |
| Cremophor ® RH 40 [1] | 1.5% |

[1] Ethoxylated hydrogenated castor oil with 40 EO units

Production:

1.8 kg of polyvinylpyrrolidone of K value 30 were dissolved in 8.0 kg of water and then 3.0 kg of kaolin and 1.05 kg of titanium dioxide were introduced. This coarse dispersion was ground in a ball mill with milling elements of 0.8-1.25 mm for 2.5 h to result in an average particle size of 2.5 µm. This pigment suspension was introduced into a stirred solution of 4.0 kg of polyvinyl alcohol-polyethylene glycol graft copolymer and 0.15 kg of Cremophor RH 40 in 22.0 kg of water. Drying took place in a fluidized bed dryer at an inlet air temperature of 90° C. Free-flowing powders with particle sizes of 315 µm were obtained.

Use

The spray suspension was produced by stirring the preparation by means of a paddle stirrer into water to result in a spray preparation with a solids content of 30%.

Dissolution or dispersion was complete after 7 min. The spray suspension was of low viscosity and homogeneous. The particle size of the pigment particles after redispersion was 2.3 µm.

The spray suspension was sprayed in a horizontal drum coater (24" Accela-Cota) onto 5 kg of caffeine tablets of the following composition:

| | |
|---|---|
| Caffeine | 50 mg |
| Ludipress (BASF AG) | 229 mg |
| Microcrystalline cellulose [1] | 40 mg |
| Crospovidone | 10 mg |
| Magnesium stearate | 1 mg |
| Total weight | 330 mg |
| Diameter: 9 mm, biconvex | |

[1] Average particle size 100 µm

Spraying Conditions:

| | |
|---|---|
| Inlet air temperature | 70° C. |
| Outlet air temperature | 41° C. |
| Spraying rate | 48 g/min |
| Spraying pressure | 0.45 MPa |

-continued

| Amount applied | 600 g of spray dispersion equivalent to 180 g of solid |
|---|---|
| Spraying time | 12.5 min |

Film-Coated Tablet Properties:

| Resistance to crushing | 131N |
|---|---|
| Friability | 0% |
| Disintegration time | 2:48 (min:s) |
| Release | 20 min: 100% |

The coating was smooth, uniform and homogeneous. The imprint was nicely reproduced without blurring effects or bridge formation. No prolongation of the disintegration time or of active ingredient release compared with the core was to be found. The resistance to crushing was 26 N higher than for the core. No changes in the properties of the film-coated tablets were found during a stability test lasting 12 months.

Example 4

Composition of the Film Coating

| Polyvinyl alcohol-polyethylene glycol 6000 (75:25) graft copolymer (degree of hydrolysis 94 mol %) | 53.5% |
|---|---|
| Vinylpyrrolidone-vinyl acetate 6:4 copolymer (copolyvidone) | 7.5% |
| Sodium dihydrogen phosphate | 1% |
| Titanium dioxide | 35% |
| Poloxamer 188 (Lutrol F 68) | 1.25% |
| Polydimethylsiloxane (simethicone) | 0.25% |
| Quinoline yellow lake | 1.5% |

Production:

All the ingredients were stirred into water, using a straight-arm stirrer, in direct succession in the sequence determined above to result in a solids concentration of 30%. This dispersion was ground using a Coruma-type rotor-stator dispersing unit for 2 h to an average particle size of 1.5 µm and then spray dried at an inlet air temperature of 120° C. to result in a free-flowing powder with particle sizes of 110 µm.

Use 160.0 g of the preparation were stirred by means of a paddle stirrer into 480.0 g of water. Dissolution or dispersion was complete after 5 min. The spray suspension was of low viscosity and homogeneous. The particle size of the pigment particles after redispersion was 1.3 µm.

The spray-suspension was sprayed in a horizontal drum coater (24" Accela-Cota) onto 5 kg of propranolo HCl tablets of the following composition:

| Propranolol HCl | 50 mg |
|---|---|
| Ludipress (BASF AG) [1] | 97.5 mg |
| Copolyvidone | 12.5 mg |
| Microcrystalline cellulose [2] | 97.5 mg |
| Magnesium stearate | 2.5 mg |
| Total weight | 260 mg |

Diameter: 9 mm, biconvex
[1] Formulated product of 93% by weight lactose, 3.5% by weight povidone and 3.5% by weight crospovidone
[2] Average particle size 100 µm Spraying Conditions:

| Inlet air temperature | 65° C. |
|---|---|
| Outlet air temperature | 35° C. |
| Spraying rate | 45 g/min |
| Spraying pressure | 0.4 MPa |
| Amount applied | 640 g of spray dispersion, equivalent to 160 g of solid |
| Spraying time | 14 min |

Film-Coated Tablet Properties:

| Resistance to crushing | 110N |
|---|---|
| Friability | 0% |
| Disintegration time | 3:15 (min:s) |
| Release | 20 min: 100% |

The coating was smooth, uniform and homogeneous. The imprint was nicely reproduced without blurring effects or bridge formation. No prolongation of the disintegration time or of active ingredient release compared with the core was to be found. The resistance to crushing was 26 N higher than for the core. No changes in the properties of the film-coated tablets were found during a stability test lasting 12 months.

Example 5

10.0 kg of the white preparation from example 1 were mixed with 0.5 kg of very finely ground red iron oxide in a ploughshare mixer for 15 min and compacted in a Gerteis roller compactor under a force of 3 kN and with a slit width of 3 mm, and the resulting compact was passed through a sieve with a mesh width of 1.0 mm. The preparation produced in this way dispersed in water within 8 min to give a fine stable dispersion. The latter was sprayed onto tablets in analogy to example 1.

The coating was smooth, uniform and homogeneous. The imprint was nicely reproduced without blurring effects or bridge formation. No prolongation of the disintegration time or of active ingredient release compared with the core was to be found.

Example 6

150 g of the white preparation from example 2 were dispersed in 470 g of water with stirring. Immediately thereafter, a liquid color premix consisting of 6 g of indigotine lake, 1 g of poloxamer 188 and 10 g of water was stirred into this dispersion. After stirring for 10 min, the preparation was ready for spraying and was sprayed onto tablets in analogy to example 2.

The coating was smooth, uniform and homogeneous. The imprint was nicely reproduced without blurring effects or bridge formation. No prolongation of the disintegration time or of active ingredient release compared with the core was to be found. No changes in the properties of the film-coated tablets were found during a stability test lasting 12 months.

We claim:

1. A rapidly dispersible, fine-particle film-coating composition which is in powder form and is not prone to segregation for coating pharmaceutical dosage forms, comprising:
    a) 40-90% by weight of a polyvinyl alcohol-polyether graft copolymer (component A),
    b) 1-20% by weight of a polyvinylpyrrolidone or of a vinylpyrrolidone-vinyl acetate-copolymer with a K value of from 10 to 100 (component B)

c) 10-60% by weight of organic or inorganic pigment particles having an average pigment particle size of less than 8 µm (component C)
d) 0.5-15% by weight of a surfactant having an HLB of greater than 10 (component D) and
e) 0-30% by weight of additional coating ingredients (components E),
in which the pigment particles of component C are completely surrounded by water soluble polymer, where the total amount of components A to E is 100% by weight.

2. The film-coating composition according to claim 1, wherein component B has a K value between 12 and 60.

3. The film-coating composition according to claim 1, wherein component B has a K value between 20 and 50.

4. The film-coating composition according to claim 1, wherein component B is a polyvinylpyrrolidone with a K value between 25 and 35 or a vinylpyrrolidone-vinyl acetate copolymer in the ratio 6:4 with a K value between 20 and 40.

5. The film-coating composition according to claim 1, wherein component C has the average pigment particle size of less than 6 µm.

6. The film-coating composition according to claim 1, wherein component C has the average pigment particle size of less than 4 µm.

7. The film-coating composition according to claim 1, wherein component C is selected from the group consisting of aluminum silicates, magnesium silicates, magnesium aluminum silicates, iron oxide, titanium dioxide, zinc oxide, silica, organic lakes and mixtures thereof.

8. The film-coating composition according to claim 1, wherein component C is selected from the group consisting of talc, kaolin, titanium dioxide, iron oxide and mixtures thereof.

9. The film-coating composition according to claim 1, wherein component D is at least one selected from the group consisting of alkali metal salts of fatty acids, alkylsulfonates, alkyl sulfates or alkylarylsulfonates, ethoxylates of fatty acids, fatty alcohols, fatty acid glycerides, sorbitan fatty acid esters, sorbitan fatty alcohol ethers, phenols and polyoxypropylene-polyoxyethylene block copolymers.

10. The film-coating composition according to claim 1, wherein sodium lauryl sulfate is employed as component D.

11. The film-coating composition according to claim 1, wherein component A is present in a concentration of 50-80% by weight.

12. The film-coating composition according to claim 1, wherein component B is present in a concentration of 2-15% by weight.

13. The film-coating composition according to claim 1, wherein component B is present in a concentration of 5-10% by weight.

14. The film-coating composition according to any claim 1, wherein component C is present in a concentration of 15-50% by weight.

15. The film-coating composition according to claim 1, wherein component C is present in a concentration of 20-45% by weight.

16. The film-coating composition according to claim 1, wherein talc or kaolin in a concentration of 5-30% by weight and titanium dioxide in a concentration of 10-40% by weight are employed as component C.

17. The film-coating composition according to claim 1, wherein component D is present in a concentration of 0.5-10% by weight.

18. The film-coating composition according to claim 1, wherein component D is present in a concentration of 1-5% by weight.

19. The film-coating composition according to claim 1, comprising
a) 60-65% by weight of a polyvinyl alcohol-polyether graft copolymer (component A),
b) 5-10% by weight of a vinylpyrrolidone-vinyl acetate copolymer (component B)
c) 14-18% by weight of talc or kaolin having the average pigment particle size of less than 8 µm, and 12-16% by weight of titanium dioxide having the average pigment particle size of less than 8 µm (component C) and
d) 1-3% by weight of sodium lauryl sulfate (component D).

20. The film-coating composition according to claim 1, wherein water-soluble colorants, non-stick agents, fillers, gloss improvers, antifoams, protective colloids, buffer substances, pH-regulating substances, bonding agents or plasticizers are employed as components E.

21. The film-coating composition according to claim 1, wherein the individual components are intimately associated with one another and cannot be separated by sieving or sifting.

22. The film-coating composition according to claim 1, wherein the average particle size of the pigment particle is less than 8 µm after redispersion in water by stirring.

23. The film-coating composition according to claim 1, wherein the average particle size of the pigment particle is less than 6 µm after redispersion in water by stirring.

24. The film-coating composition according to claim 1, wherein the average particle size of the pigment particle is less than 4 µm after redispersion in water by stirring.

25. The film-coating composition according to claim 1, wherein the average particle size of the powder is greater than 50 µm.

26. The film-coating composition according to claim 1, wherein the average particle size of the powder is greater than 100 µm.

27. The film-coating composition according to claim 1, wherein the average particle size of the powder is greater than 150 µm.

28. A process for producing a film-coating composition according to claim 1, which comprises grinding component C in water to the required particle size, combining with the other components and, optionally additional water, and drying the resulting aqueous dispersion.

29. A process for producing a film-coating composition according to claim 1, which comprises grinding component C in water in the presence of component A, component B, component D or component E or combinations thereof to the required particle size, combining with the remaining components and, optionally additional water, and drying the resulting aqueous dispersion.

30. A process for producing a film-coating composition according to claim 1, which comprises grinding component C in water in the presence of components B and D and, optionally, E to the required particle size, combining with an aqueous solution of component A and, optionally additional water, and drying the resulting aqueous dispersion.

31. A process for producing a film-coating composition according to claim 1, wherein component C is ground in water in the presence of complete quantities or partial quantities of components A, B, D or E or combinations thereof to the required particle size, drying to a powder or granules, and mixing with the remaining quantities of component A, B, D and E in powder form.

32. A process for producing a film-coating composition according to claim 1, which comprises grinding component C in water in the presence of components B, D or E or combinations thereof to the required particle size, drying the resulting aqueous dispersion and mixing with component A in powder form.

33. The process according to claim 28, wherein the drying of the aqueous dispersion takes place by spray drying, fluidized bed drying, drum drying or spray granulation.

34. The process according to claim 33, wherein the spray drying takes place at inlet air temperatures of 60-200° C.

35. The process according to claim 34, wherein the atomization of the suspension in the spray drying takes place at pressures greater than 0.1 MPa.

36. The process according to claim 28, wherein the product obtained in powder form after drying of the aqueous dispersion is mixed with further coloring components in powder form and, optionally, compacted, extruded, pelleted or granulated.

37. The process according to claim 28, wherein a film-coating composition which is in powder form and comprises only white pigments is mixed with coloring components in powder form and, optionally, compacted, extruded, pelleted or granulated.

38. A process for producing coated pharmaceutical dosage forms, which comprises stirring a film-coating composition according to claim 1 into water, mixing with additional components and applying to a substrate by means of a suitable spraying device, with successive drying of the film coating by feeding in heated air.

39. A solid pharmaceutical dosage form coated with the film-coating composition according to claim 1.

40. A solid pharmaceutical dosage form according to claim 39, which comprises as active ingredients medicinal substances, vitamins, carotenoids, minerals, dietary supplements or trace elements.

41. A solid pharmaceutical dosage form according to claim 39, wherein tablets, extrudates or capsules are provided with a film coating.

42. A rapidly dispersible, fine-particle film-coating composition which is in powder form and is not prone to segregation for coating pharmaceutical dosage forms, comprising:
   a) 40-90% by weight of a polyvinyl alcohol-polyether graft copolymer (component A),
   b) 1-20% by weight of a polyvinylpyrrolidone or of a vinylpyrrolidone-vinyl acetate-copolymer with a K value of from 10 to 100 (component B)
   c) 10-60% by weight of organic or inorganic pigment particles having an average pigment particle size of less than 8 µm (component C)
   d) 0.5-15% by weight of a surfactant having an HLB of greater than 10 (component D) and
   f) 0-30% by weight of additional coating ingredients (components E), in which the pigment particles of component C are completely surrounded by water-soluble polymer,
where the total amount of components A to E is 100% by weight; wherein the composition is made in a process consisting of:
   A) grinding component C in water to the required particle size, combining with the other components and, optionally additional water, and drying the resulting aqueous dispersion, or
   B) grinding component C in water in the presence of component A, component B, component D or component E or combinations thereof to the required particle size, combining with the remaining components and, optionally additional water, and drying the resulting aqueous dispersion, or
   C) grinding component C in water in the presence of components B and D and, optionally, E to the required particle size, combining with an aqueous solution of component A and, optionally additional water, and drying the resulting aqueous dispersion, or
   D) grinding component C in water in the presence of complete quantities or partial quantities of components A, B, D or E or combinations thereof to the required particle size, drying to a powder or granules, and mixing with the remaining quantities of component A, B, D and E in powder form, or
   E) grinding component C in water in the presence of components B, D or E or combinations thereof to the required particle size, drying the resulting aqueous dispersion and mixing with component A in powder form.

43. A rapidly dispersible, fine-particle film-coating composition which is in powder form and is not prone to segregation for coating pharmaceutical dosage forms, consisting of:
   a) 40-90% by weight of a polyvinyl alcohol-polyether graft copolymer (component A),
   b) 1-20% by weight of a polyvinylpyrrolidone or of a vinylpyrrolidone-vinyl acetate-copolymer with a K value of from 10 to 100 (component B)
   c) 10-60% by weight of organic or inorganic pigment particles having an average pigment particle size of less than 8 µm (component C)
   d) 0.5-15% by weight of a surfactant having an HLB of greater than 10 (component D) and
   g) 0-30% by weight of additional coating ingredients (components E) selected from the group consisting of water-soluble colorants, non-stick agents, fillers, gloss improvers, antifoams, protective colloids, buffer substances, pH-regulating substances, bonding agents, and combinations thereof, in which the pigment particles of component C are completely surrounded by water-soluble polymer.

* * * * *